United States Patent [19]

Yamaguchi et al.

[11] Patent Number: 5,168,877
[45] Date of Patent: Dec. 8, 1992

[54] ULTRASONIC DIAGNOSTIC APPARATUS

[75] Inventors: Keiki Yamaguchi; Yuichi Hirota; Takao Jibiki, all of Tokyo, Japan

[73] Assignee: Yokogawa Medical Systems, Limited, Tokyo, Japan

[21] Appl. No.: 689,056

[22] PCT Filed: Oct. 31, 1989

[86] PCT No.: PCT/JP89/01128
§ 371 Date: May 28, 1991
§ 102(e) Date: May 28, 1991

[87] PCT Pub. No.: WO90/04946
PCT Pub. Date: May 17, 1990

[30] Foreign Application Priority Data
Oct. 31, 1988 [JP] Japan .................. 63-273191

[51] Int. Cl.[5] .............................. A61B 8/12
[52] U.S. Cl. ................... 128/661.09; 128/661.08
[58] Field of Search .............. 128/661.08, 661.09, 128/661.10, 662.02

[56] References Cited

U.S. PATENT DOCUMENTS

| | | | |
|---|---|---|---|
| 4,911,171 | 3/1990 | Uchibori | 128/661.09 |
| 4,955,386 | 9/1990 | Nishiyama et al. | 128/661.09 |
| 4,993,417 | 2/1991 | Seo | 128/661.09 |

Primary Examiner—Kyle L. Howell
Assistant Examiner—George Manuel
Attorney, Agent, or Firm—Moonray Kojima

[57] ABSTRACT

An object of the present invention is to obtain an ultrasonic diagnostic apparatus including a CFM system which is designed so that the algorithm for computing a flow velocity or the like can be changed easily.

The ultrasonic diagnostic apparatus according to the present invention comprises an A/D converter that converts a Doppler signal obtained by coherent detection of the echo reflected from an object of inspection into a digital signal, and a flow velocity computing section that determines a blood flow velocity and velocity dispersion on the basis of the Doppler signal from the A/D converter. The flow velocity computing section includes an MTI filter and a computing unit that determines a blood flow velocity and velocity dispersion by processing an output signal from the filter, both the MTI filter and the computing unit comprising respective digital signal processors (DSPs).

1 Claim, 1 Drawing Sheet

ULTRASONIC DIAGNOSTIC APPARATUS

DESCRIPTION

1. Technical Field

The present invention relates to an ultrasonic diagnostic apparatus having a blood flow imaging function of displaying, for example, the blood flow velocity in colors.

2. Background Art

One type of ultrasonic diagnostic apparatus having a so called color flow mapping (hereinafter referred to as "CFM") function, which enables the blood flow to be imaged using a different color for each particular blood flow velocity, is spreading rapidly because it permits the blood flow velocity to be determined easily. According to the CFM, scanning is effected with an ultrasonic beam while repeating the transmission and reception of an ultrasonic wave a minimal number of times for one direction, thereby displaying a two-dimensionally extending blood flow image.

Such an ultrasonic diagnostic apparatus includes a pulsed Doppler computing circuit that outputs a Doppler signal from a received signal obtained through a transmitting-receiving circuit, and a flow velocity computing section that determines a blood flow velocity, for example, on the basis of the Doppler signal. However, since the flow velocity computing section comprises a digital computing circuit that is for the exclusive use of it, the computing algorithm is fixedly determined by the circuit configuration and hence lacking in flexibility. Therefore, when the computing algorithm needs to be changed, the hardware configuration itself must be changed.

DISCLOSURE OF INVENTION

The present invention aims at solving the above-described problems, and it is an object of the present invention to obtain an ultrasonic diagnostic apparatus including a CFM system which is designed so that the computing algorithm can be changed easily in accordance with technical advance or a change in specifications.

The ultrasonic diagnostic apparatus according to the present invention comprises an A/D converter that converts a Doppler signal obtained by coherent detection of the echo reflected from an object of inspection into a digital signal, and a flow velocity computing section that determines a blood flow velocity and velocity dispersion on the basis of the Doppler signal from the A/D converter. The flow velocity computing section includes an MTI filter and a computing unit that determines a blood flow velocity and velocity dispersion by processing an output signal from the filter, both the MTI filter and the computing unit comprising respective digital signal processors (DSPs).

BRIEF DESCRIPTION OF THE DRAWINGS

The figure is a block diagram showing the arrangement of an ultrasonic diagnostic apparatus according to one embodiment of the present invention.

BEST MODE FOR CARRYING OUT THE INVENTION

Figure 1:
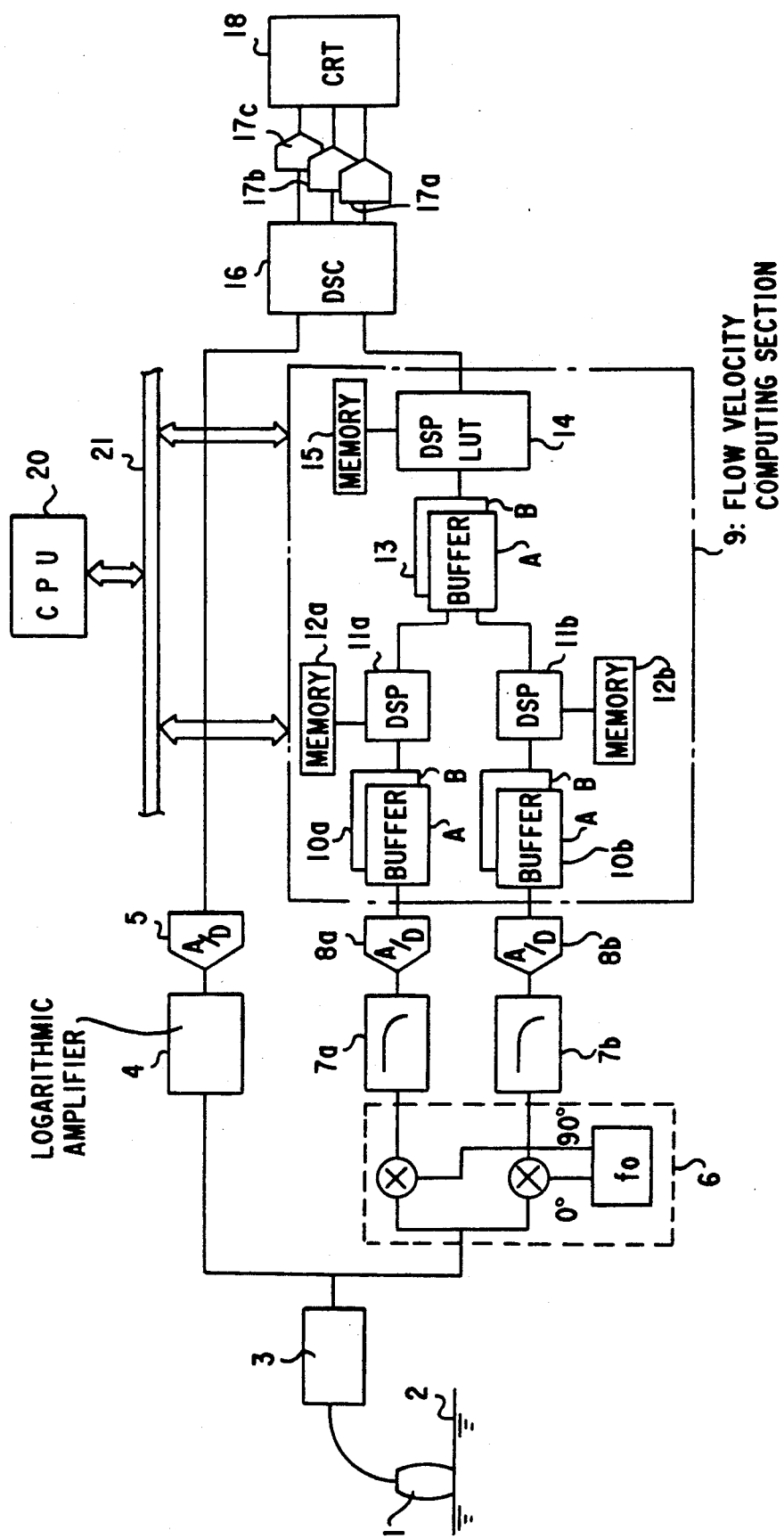

FIG. 1 is a block diagram showing the arrangement of an essential part of an ultrasonic diagnostic apparatus according to one embodiment of the present invention. In the figure, reference numeral 1 denotes a probe that sends out an ultrasonic signal into an object 2 of inspection and receives an echo signal reflected from the object 2, and 3 a transmitting-receiving circuit that drives the probe 1 and also receives the echo signal. A logarithmic amplifier circuit 4 logarithmically amplifies the echo signal received by the transmitting receiving circuit 3, and an analog-to-digital converter (hereinafter referred to as "A/D converter") 5 converts the echo signal (analog signal) amplified in the logarithmic amplifier circuit 4 into a digital signal. The logarithmic amplifier 4 and the A/D converter 5 constitute a B-mode signal processing system.

A Doppler demodulator circuit 6 divides the received signal into two-channel signals, which are multiplied by respective reference waves which are 90° out of phase with each other to detect a Doppler signal. Reference numerals 7a and 7b denote low-pass filters, and 8a and 8b A/D converters.

A flow velocity computing section 9 includes buffer memories 10a and 10b that alternately store signals from the A/D converters 8a and 8b for each sound ray. Reference numerals 11a and 11b denote digital signal processors, and 12a and 12b memories for storing programs and data which are utilized in the respective digital signal processors 11a and 11b. The digital signal processors 11a and 11b and the memories 12a and 12b constitute an MTI (Moving Target Indicator) filter. As each of the digital signal processors 11a and 11b, for example, a digital signal processor 320C25, which is an LSI manufactured by TI, may be employed. Such a digital signal processor is commonly known as "DSP". The memories 12a and 12b are connected to a superior CPU 20 by a bus 21, through which a program and data are loaded thereinto from the CPU 20. The MTI filter suppresses an echo signal from an immobile portion of the object 2 to extract an echo signal only from a moving portion of the object 2.

A buffer memory 13 alternately stores signals from the MTI filter for each sound ray. A computing circuit 14 determines a blood flow velocity, blood flow velocity dispersion, etc. from the Doppler signal. The computing circuit 14 includes a digital signal processor DSP, a look-up table LUT that is stored with various kinds of data, and so forth. The digital signal processor DSP executes a predetermined arithmetic processing for determining a blood flow velocity, blood flow velocity dispersion, etc. from the Doppler signal on the basis of a program and data stored in a memory 15. The memory 15 is also connected to the CPU 20 through the bus 21 so that a program and data are loaded thereinto from the CPU 20. It is assumed that each digital signal processor DSP in the velocity computing section 9 is connected by a pipeline structure. Reference numeral 16 denotes a digital scan converter (hereinafter referred to as "DSC"), 17a, 17b and 17c digital-to-analog converters (hereinafter referred to as "D/A converters") for converting an echo signal or the like, which is a digital signal, into an analog signal, and 18 a color monitor.

The operation of the ultrasonic diagnostic apparatus arranged as described above will be explained below.

First, an ultrasonic wave is transmitted to the object 2 at a predetermined timing from the probe 1. Receiving an echo signal reflected from the interior of the object 2, the probe 1 outputs the received signal to the transmitting-receiving circuit 3. In correspondence with the intermittent transmission of the ultrasonic signal into the object 2, the transmitting-receiving circuit 3 alternately outputs the echo signal to the logarithmic amplifier circuit 4 and the Doppler demodulator circuit 6.

The logarithmic amplifier circuit 4 logarithmically amplifies the echo signal and outputs the amplified signal to the A/D converter 5. The A/D converter 5 converts the logarithmically amplified echo signal into a digital signal. This digital echo signal is used to effect B-mode imaging. On the other hand, the Doppler demodulator 6 subjects the echo signal to Doppler demodulation to obtain Doppler signals and outputs them to the A/D converters 8a and 8b rough the low-pass filters 7a and 7b.

The Doppler signals which are converted into digital signals in the A/D converters 8a and 8b are temporarily stored for each sound ray in each of the memories A and B of the buffer memories 10a and 10b. When Doppler signals for one sound ray have been stored in each of the memories A and B of the buffer memories 10a and 10b, the MTI filter applies a predetermined signal processing to the Doppler signals for each sound ray and then sends them to the buffer memory 13. In this buffer memory 13 also, signals are temporarily stored in each of the memories A and B for each sound ray. The computing circuit 14 determines a blood flow velocity, blood flow velocity dispersion, etc. on the sound ray corresponding to the echo signal on the basis of the signals stored in the buffer memory 13 and outputs the result of the computation to the DSC 16.

The DSC 16 executes coordinate transformation on the basis of the echo signal output from the A/D converter 5 and the result of the computation by the computing circuit 13 and outputs the resulting signals to the D/A converters 17a, 17b and 17c. The D/A converters 17a, 17b an 17c convert these signals into analog signals and then outputs them to the color monitor 18. The color monitor 18 performs B-mode imaging and displays CFM.

Although the computing operations that are executed by the MTI filter (11a, 12a; and 11b, 12b) and the computing unit 14 per se are the same as those in the conventional apparatus, in this embodiment each of these units comprises a digital signal processor DSP and therefore the signal processing speed is high and it is also possible to readily cope with a change in the computing algorithm by loading a program and the like into the memories of these units from the superior CPU.

Thus, the present invention, in which digital signal processors are employed to compute a blood flow velocity and the like, makes it possible to readily cope with a change in the computing algorithm.

What is claimed is:

1. In an ultrasonic diagnostic apparatus comprising
   an analog to digital converter for converting into a digital signal a Doppler signal obtained by detecting an echo signal reflected from an object being examined;
   a blood flow detecting means for detecting blood flow velocity and dispersion of the object based on the digital Doppler signal from said analog to digital converter and for outputting a first output signal representing said blood flow velocity and dispersion; and
   display means, responsive to said first output signal, for displaying in color the blood flow velocity and dispersion;
   the improvement comprising
   said blood flowing detecting means comprising
      a moving target indicator means consisting of a first memory having a readily replaceable content and connected to a central processing unit and a first digital signal processor for receiving said digital Doppler signal from said analog to digital converter and, utilizing the contents of said first memory, for generating a second output signal; and
      computing means consisting of a second memory having a readily replaceable content and connected to said central processing unit and a second digital signal processor for receiving said second output signal, and, utilizing the contents of said second memory, for generating said first output signal representing the blood flow velocity and dispersion, said first output signal being outputted to said display means,
      whereby said central processing unit replaces the contents of said first memory and said second memory so that the processing speed is increased and computing flexibility is attained.

* * * * *